US00PP24193P2

(12) United States Plant Patent
Traven

(10) Patent No.: US PP24,193 P2
(45) Date of Patent: Jan. 21, 2014

(54) ***LAVANDULA* PLANT NAMED 'NIKO'**

(50) Latin Name: *Lavandula angustifolia*
Varietal Denomination: Niko

(76) Inventor: Lloyd R. Traven, Kintnersville, PA (US)

( * ) Notice: Subject to any disclaimer, the term of this patent is extended or adjusted under 35 U.S.C. 154(b) by 61 days.

(21) Appl. No.: 13/317,618

(22) Filed: Oct. 24, 2011

(51) Int. Cl.
*A01H 5/00* (2006.01)

(52) U.S. Cl.
USPC ..... Plt./445; Plt./226

(58) Field of Classification Search
USPC ..... Plt./445, 226
See application file for complete search history.

*Primary Examiner* — June Hwu

(57) ABSTRACT

A new cultivar of *Lavandula* plant named 'Niko' that is characterized by flower spikes with purple flowers, a round shape with a compact habit, foliage that does not dieback in the center of the plant, a long period of field production and strong resistance to both Summer and Winter *pythium* species.

2 Drawing Sheets

Botanical classification: *Lavandula angustifolia.*
Variety denomination: 'Niko'.

BACKGROUND OF THE INVENTION

The present invention relates to a new and distinct cultivar of *Lavandula* plant botanically known as *Lavandula angustifolia* and hereinafter referred to by the cultivar name 'Niko'.

'Niko' was discovered as a whole plant mutation of *Lavandula* 'Grosso'. 'Niko' was discovered as a single plant in a bed of *Lavandula* 'Grosso' plants in 2007 in a cultivated area of Kintnersville, Pa.

Asexual reproduction of the new cultivar 'Niko' first occurred by terminal cuttings in 2007 in Kintnersville, Pa. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Lavandula* cultivar 'Niko'. These traits in combination distinguish 'Niko' as a new and distinct cultivar apart from other existing known varieties of *Lavandula.*

1. *Lavandula* 'Niko' exhibits flower spikes with purple flowers.
2. *Lavandula* 'Niko' exhibits a compact habit.
3. *Lavandula* 'Niko' exhibits a round shape.
4. *Lavandula* 'Niko' exhibits foliage that does not dieback in the center of the plant.
5. *Lavandula* 'Niko' exhibits a long period of field production.
6. *Lavandula* 'Niko' exhibits strong resistance to both Summer and Winter *pythium* species.

The closest comparison cultivar is *Lavandula* 'Grosso' (not patented). 'Niko' is distinguishable from 'Grosso' by the following characteristics:

1. 'Niko' has a more compact and rounded habit than 'Grosso'.
2. 'Niko' has no foliage dieback in the center. The leaves of 'Grosso' experience dieoff in the center of the plant.

3. 'Niko' has a longer period of field production than 'Grosso'.

In comparison to *Lavandula* 'Hidcote' (not patented), 'Niko' is distinguishable from 'Hidcote' by the following characteristics:

1. 'Niko' has a smaller overall size than 'Hidcote'.
2. 'Niko' has shorter lateral branches than 'Hidcote'.
3. 'Niko' has smaller flower spikes than 'Hidcote'.
3. 'Niko' has lighter purple colored flowers than 'Hidcote'.

BRIEF DESCRIPTION OF THE DRAWING

The accompanying photographs illustrate the distinguishing traits of *Lavandula* 'Niko'.

The plant in the photograph of sheet 1 shows an overall view of a 1 year old plant.

Sheet 2 shows a close up view of a flower spike.

The photographs were taken using conventional techniques and although colors may appear different from actual colors due to light reflectance it is as accurate as possible by conventional photographic techniques.

BOTANICAL DESCRIPTION OF THE PLANT

The following is a detailed description of the new *Lavandula* cultivar named 'Niko'. Data was collected in Mainz, Germany from 1 year old plants grown outdoors in 16 cm. diameter containers. The time of year was Summer and the average temperature was 15 to 30 degrees Centigrade during the day and 12 to 20 degrees Centigrade at night. The light level was natural light. No photoperiodic treatments or growth retards were used. Color determinations are in accordance with The Royal Horticultural Society Colour Chart 2007 edition, except where general color terms of ordinary dictionary significance are used. The growing requirements are similar to the species. 'Niko' has not been tested under all possible conditions and phenotypic differences may be observed with variations in environmental, climatic, and cultural conditions, however, without any variance in genotype.

Botanical classification: *Lavandula angustifolia* 'Niko'. Annual or perennial: Perennial.
Parentage: 'Niko' is a whole plant mutation of *Lavandula angustifolia* 'Grosso'.
Vigor: Strong.
Growth habit: Upright.
Plant shape: Rounded, mounding.
Suitable container size: 16 cm. pots.
Height: 50 cm. in height.
Width: 50 cm. in width.
Low temperature tolerance: USDA Zone 5.
High temperature tolerance: 40° Centigrade.
Propagation: Terminal cuttings.
Time to initiate roots in summer: 16 days to initiate roots at 22° Centigrade.
Time to initiate roots in winter: 24 days to initiate roots at 20° Centigrade.
Time to produce a rooted cutting or liner in summer: 20 days at 22° Centigrade.
Time to produce a rooted cutting or liner in winter: 28 days at 20° Centigrade.
Crop time: Approximately 15 weeks.
Root system: Fine and fibrous.
Stem:
- *Basal branching.*—Yes.
- *Average number of lateral branches.*—20.
- *Pinching.*—No.
- *Lateral branch diameter.*—2.5 mm. in diameter.
- *Lateral branch length.*—12 cm. in length.
- *Internode length.*—2 cm.
- *Stem shape.*—Square.
- *Stem strength.*—Strong.
- *Stem color.*—137D.
- *Pubescence.*—Present.

Foliage:
- *Leaf arrangement.*—Opposite.
- *Compound or single.*—Single.
- *Number of leaves per lateral branch.*—8.
- *Leaf shape.*—Ligulate.
- *Leaf apex.*—Acute.
- *Leaf base.*—Cuneate.
- *Leaf length.*—5.5 cm. in length.
- *Leaf width.*—0.6 cm. in width.
- *Texture.*—Covered with short hairs on both sides.
- *Leaf margin.*—Entire.
- *Venation pattern.*—Pinnate.
- *Young leaf color* (*upper surface*).—122B.
- *Young leaf color* (*lower surface*).—133D.
- *Mature leaf color* (*upper surface*).—137C.
- *Mature leaf color* (*lower surface*).—137D.
- *Vein color* (*upper surface*).—137C.
- *Vein color* (*under surface*).—137D.
- *Leaf attachment.*—Petiolate.
- *Petiole dimensions.*—2 mm. in length, and 2 mm. in diameter.
- *Petiole color.*—144D.
- *Durability of foliage to stress.*—Strong.
- *Foliage fragrance.*—Strongly scented.

Flower:
- *Inflorescence arrangement.*—Terminal and lateral verticillasters.
- *Spike shape.*—Cylindrical.
- *Inflorescence dimensions.*—4.5 cm. in length and 1.3 cm. in width.
- *Quantity of flowers per inflorescence.*—40.
- *Quantity of flowers per lateral stem.*—8 to 15 spikes.
- *Quantity of flower buds per lateral stem.*—8 to 15 spikes.
- *Quantity of flowers and buds per plant.*—50 to 70 spikes.
- *Number of harvestable stems per year.*—35 to 50.
- *Natural flowering season.*—June to July.
- *Time to flower.*—6 weeks.
- *Rate of flower opening.*—Every 3 to 4 days.
- *Fragrance.*—Strong.
- *Flower bud length.*—8 mm.
- *Flower bud diameter.*—2 mm.
- *Flower bud shape.*—Ovate.
- *Bud color.*—93B.
- *Rate of bud opening.*—3 to 4 days.
- *Flower aspect.*—Outward.
- *Flower shape.*—Labiate.
- *Flower dimensions.*—5 mm. in diameter and 6 mm. in height.
- *Flower longevity.*—5 days.
- *Number of petals.*—5.
- *Fused or unfused.*—Fused.
- *Petal arrangement.*—Zygomorphic.
- *Petal texture.*—Smooth both sides.
- *Petal shape.*—Ligulate.
- *Petal margin.*—Entire.
- *Petal apex.*—Obtuse.
- *Petal base.*—Fused.
- *Petal length.*—3 mm.
- *Petal width.*—2 mm.
- *Petal color when opening* (*upper side*).—90D.
- *Petal color when opening* (*under side*).—N87C.
- *Petal color fully opened* (*upper side*).—90D.
- *Petal color fully opened* (*under side*).—N87C.
- *Petal color fading to.*—90D.
- *Self-cleaning or persistent.*—Persistent.

Bracteoles: Absent.
Sepals:
- *Sepal arrangement.*—Fused.
- *Number of sepals.*—2.
- *Sepal shape.*—Ovate.
- *Sepal margin.*—Entire.
- *Sepal apex.*—Obtuse.
- *Sepal base.*—Fused.
- *Sepal texture.*—Slightly rough, covered with fine hairs on both sides.
- *Sepal dimensions.*—7.0 mm. in length and 2.0 mm. in width.
- *Young sepal color* (*upper side*).—N87C and 149D.
- *Young sepal color* (*under side*).—N87C and 149D.
- *Mature sepal color* (*upper side*).—N87C and 149D.
- *Mature sepal color* (*under side*).—N87C and 149D.

Calyx:
- *Calyx shape.*—Fused.
- *Calyx dimensions.*—7 mm. in length and 2 mm. in diameter.

Peduncle:
- *Peduncle dimensions.*—45 cm. in length and 3 mm. in diameter.
- *Peduncle angle.*—0 to 30 degrees from vertical.
- *Peduncle strength.*—Strong.
- *Peduncle texture.*—Slightly rough, covered with fine hairs on both sides.
- *Peduncle color.*—137C.

Reproduction organs:
- *Stamen number.*—5.
- *Anther shape.*—Ovate.

*Anther size.*—1.5 mm.
*Anther color.*—12B.
*Amount of pollen.*—High.
*Pollen color.*—12B.
*Pistil number.*—1.
*Pistil length.*—2.0 mm.
*Stigma shape.*—Reniform.
*Stigma color.*—149D.
*Style length.*—2 mm.
*Style color.*—149D.
*Ovary color.*—149D.

Seed:

*Quantity of seeds.*—3 to 5 per flower.
*Seed dimensions.*—0.5 mm. in length and 0.2 mm. in diameter.
*Seed color.*—N144A.

Disease and pest resistance: Strong resistance to both Summer and Winter *pythium* species.

The invention claimed is:

1. A new and distinct variety of *Lavandula* plant named 'Niko' as described and illustrated.

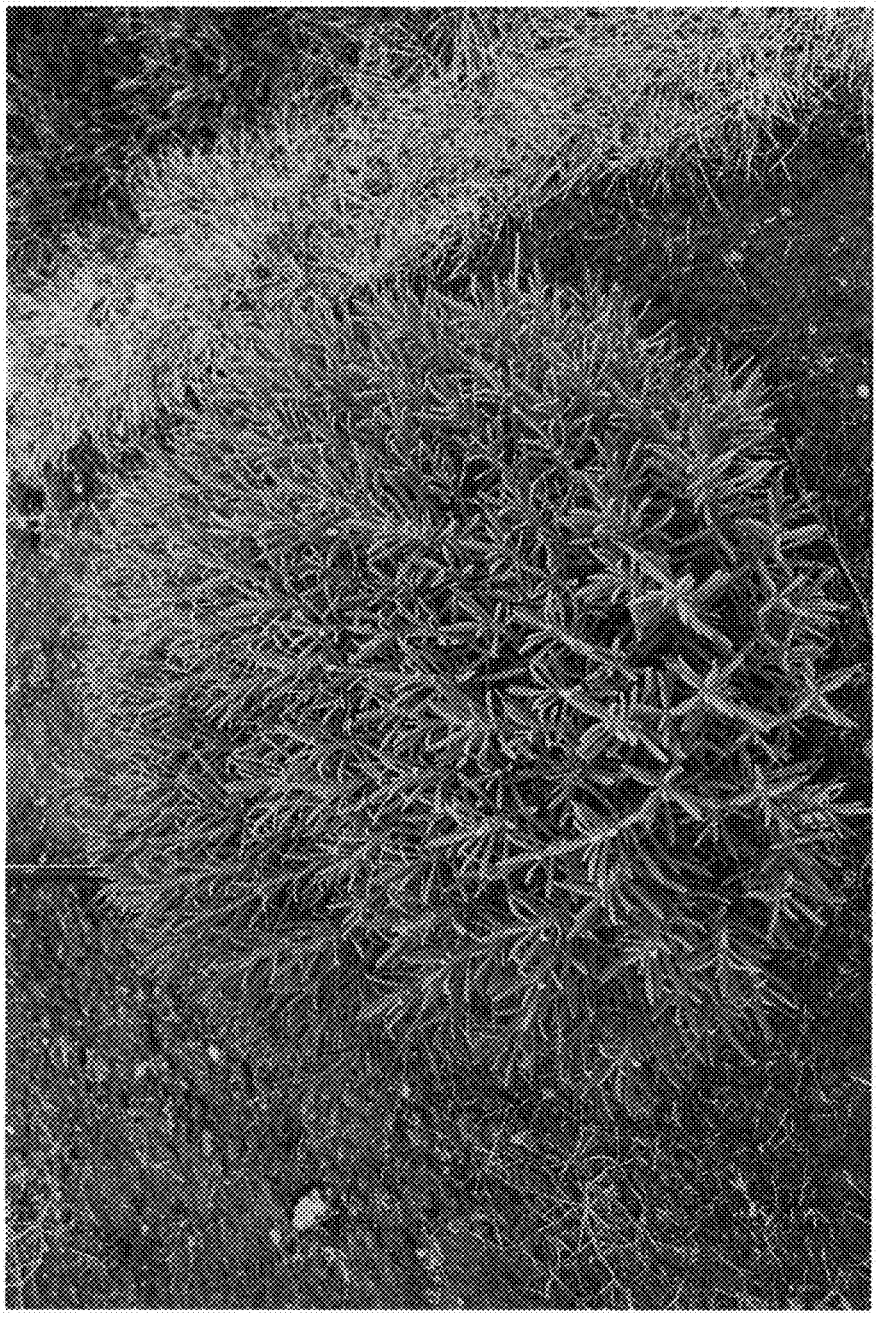

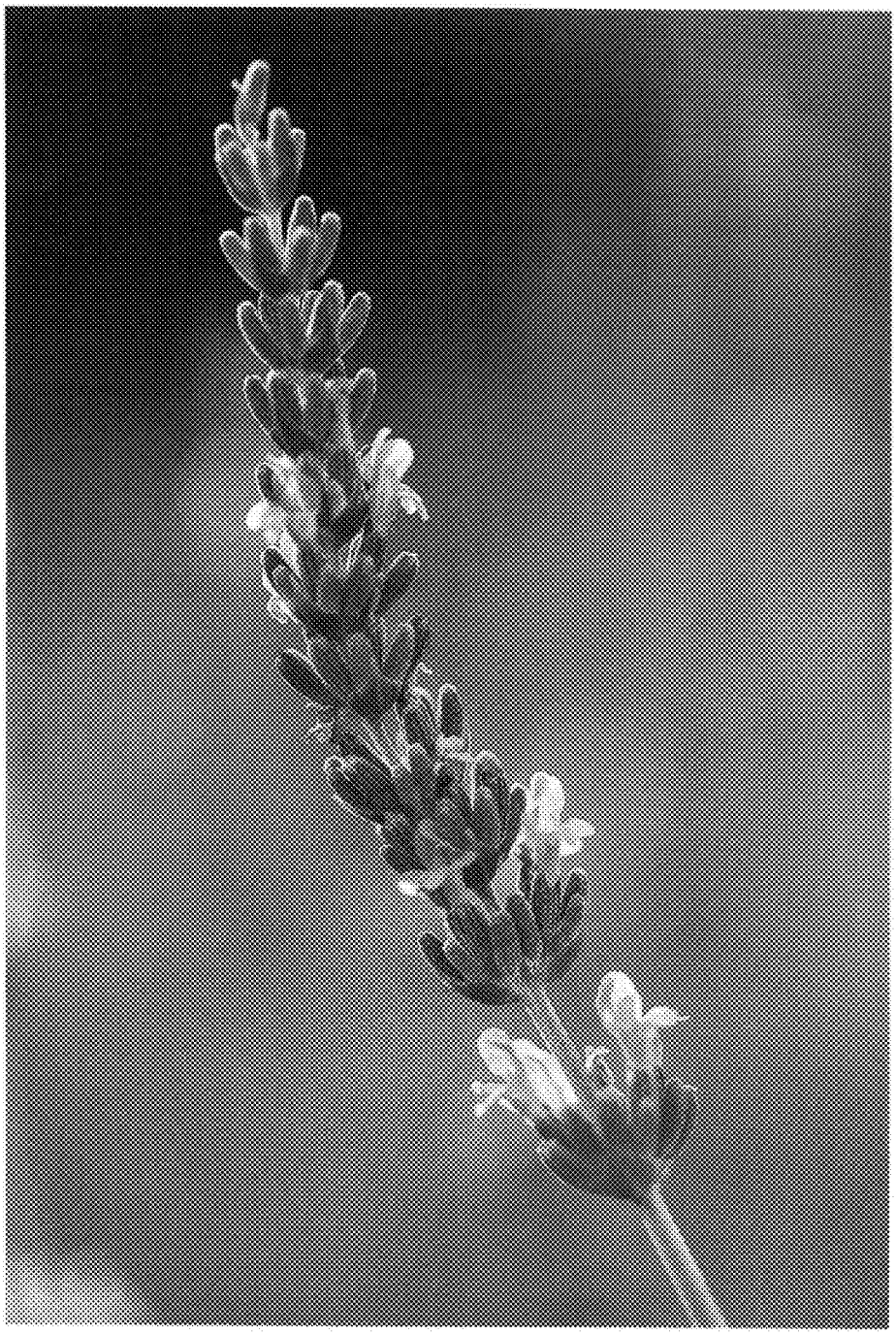

* * * * *